United States Patent [19]

Sullivan et al.

[11] 4,276,236

[45] Jun. 30, 1981

[54] APPARATUS FOR INDUCING AIR FLOW PAST A PRODUCT CAPABLE OF BEING VAPORIZED

[75] Inventors: William E. Sullivan; Murray O. Meetze, Jr., both of Columbia, S.C.

[73] Assignee: Risdon Enterprises, Inc., Columbia, S.C.

[21] Appl. No.: 117,827

[22] Filed: Feb. 4, 1980

Related U.S. Application Data

[60] Continuation of Ser. No. 900,820, Apr. 27, 1978, abandoned, which is a division of Ser. No. 732,137, Oct. 13, 1976, abandoned.

[51] Int. Cl.³ .............................................. A61L 9/04
[52] U.S. Cl. ..................................... 261/30; 261/102; 261/101; 422/305; 422/306
[58] Field of Search .......................... 21/53, 74 R, 126; 222/76; 429/96-100; 261/30, 101, 102; 422/305, 306; 206/0.5; 239/34; 220/46, 4 E, 252

[56] References Cited

U.S. PATENT DOCUMENTS

| | | | |
|---|---|---|---|
| 1,286,800 | 12/1918 | Schulte | 429/99 |
| 1,879,623 | 9/1932 | Jones | 429/99 |
| 2,081,656 | 5/1937 | Anthony | 429/99 |
| 2,333,028 | 10/1943 | Merrill | 429/99 |
| 2,718,541 | 9/1955 | Spooner | 429/97 |
| 3,181,974 | 5/1965 | Barbera | 429/100 |
| 3,990,848 | 11/1976 | Corris | 21/74 R |
| 3,993,444 | 11/1976 | Brown | 21/126 |
| 4,035,451 | 7/1977 | Tringali | 261/101 |
| 4,070,821 | 1/1978 | Somogyi | 429/99 |

Primary Examiner—Frank W. Lutter
Assistant Examiner—Gregory N. Clements
Attorney, Agent, or Firm—St. Onge, Steward, Johnston, Reens & Noë

[57] ABSTRACT

A battery-powered apparatus, for inducing air flow past a product capable of being vaporized, includes a compact housing that comprises a hollow outer shell and a hollow, generally cylindrical inner shell, having an axis, on which the operating components of the apparatus are supported. The inner shell is mounted with the outer shell by a hinge to pivot substantially on the axis between closed and open positions. In the closed position the inner shell compliments the outer shell to define an enclosed space and shield the apparatus components. In the open position, the inner shell is nested within the outer shell to expose the apparatus components. The product and a battery for powering the apparatus may be assembled into a cartridge formed to be received in the apparatus housing. Electrical battery contacts and a support for the cartridge in the housing are also disclosed.

23 Claims, 6 Drawing Figures

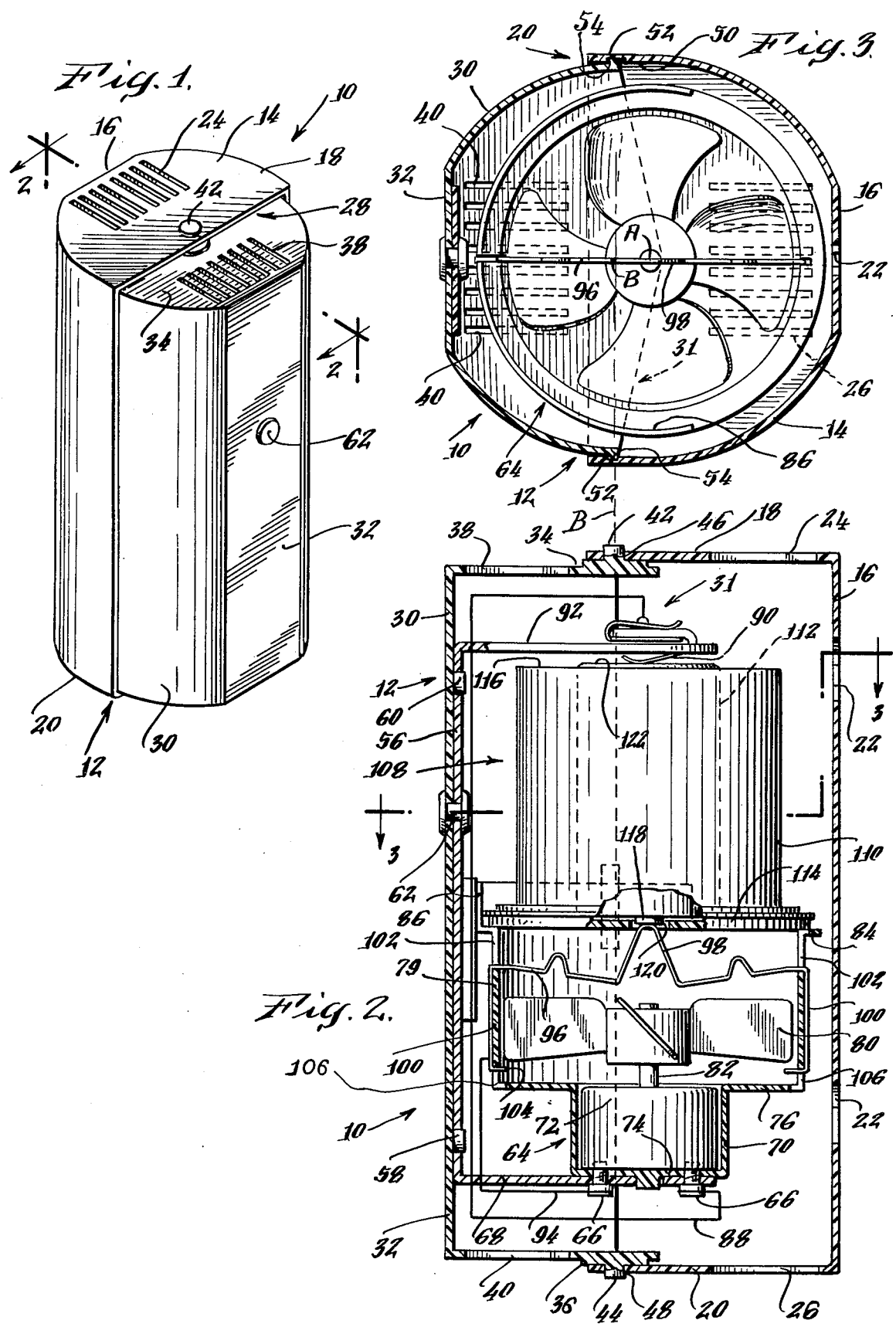

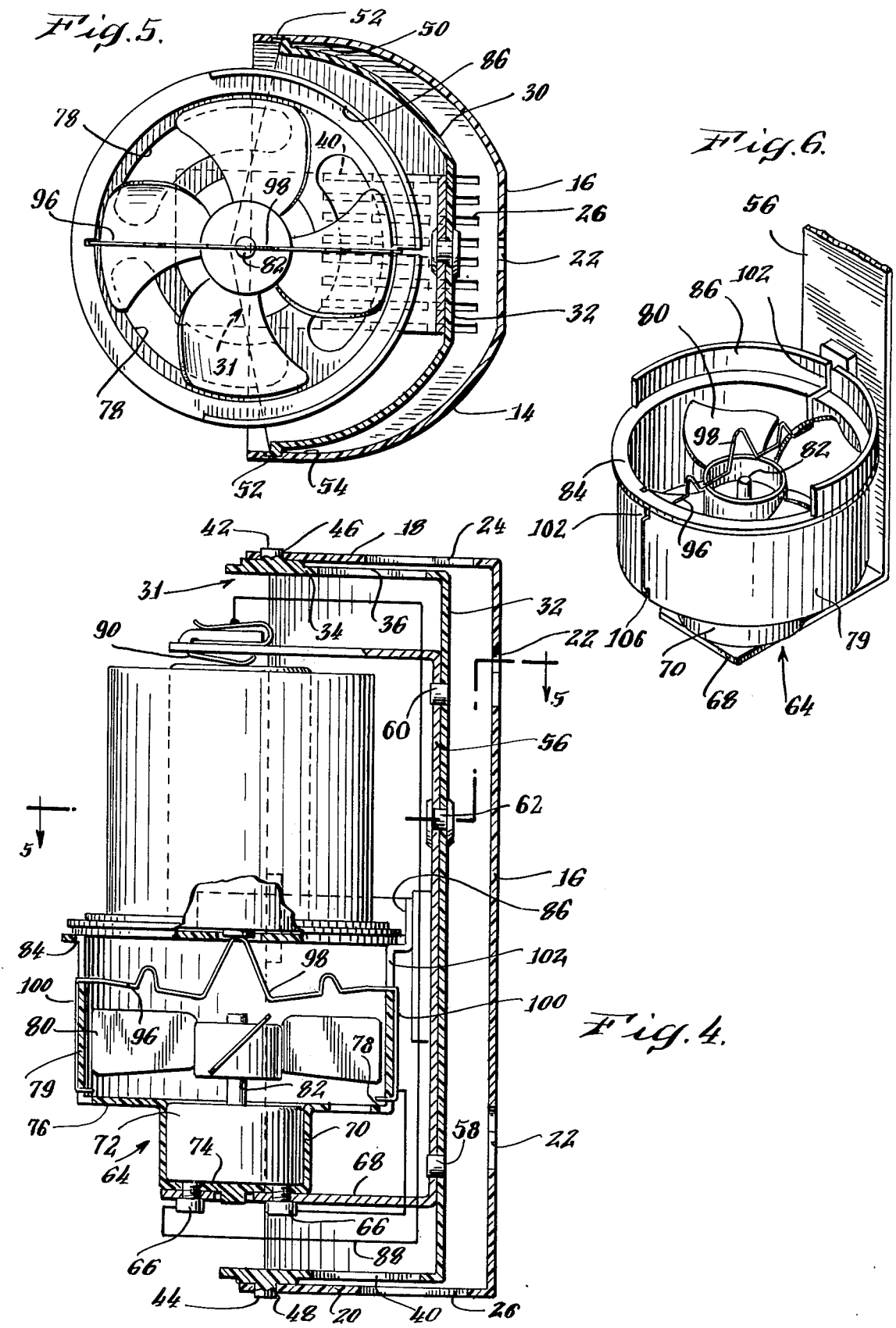

APPARATUS FOR INDUCING AIR FLOW PAST A PRODUCT CAPABLE OF BEING VAPORIZED

This is a continuation application of Application Ser. No. 900,820 filed Apr. 27, 1978 now abandoned which was a divisional application of Application Ser. No. 732,137, filed Oct. 13, 1976, now abandoned.

BACKGROUND OF THE INVENTION

1. Field of the Invention

The present invention relates to an apparatus for inducing air flow past a product which may be vaporized in order to aid distribution of the product into the environment.

Many products, such as room deodorizers, insecticides, germicides and the like, which are desirably distributed in vapor form in their environment are now manufactured in solid or semi-solid form, for example, as a gel. Products in solid or liquid form have also been impregnated in porous and microporous materials. In both packaging forms, the products are released into the environment in which they are exposed by a vaporization process such as evaporation or sublimination.

Though most products of the type described above are now used merely by exposing them in the environment to be treated, it is preferable in certain applications to induce greater distribution of the product than is possible by this technique. If an apparatus is provided to induce this greater distribution, it is desirable to house the apparatus compactly and conveniently so that when exhausted, the product can be easily replenished and so that access to the components of the apparatus may be easily provided. And the apparatus should be mountable in small areas yet still offer the above features.

2. Description of the Prior Art

Systems for inducing air currents past products which can be vaporized to assure greater and more even product distribution are known. For example, U.S. Pat. No. 3,990,848 (Corris), assigned to the assignee of the present invention, discloses a system having an apparatus which includes a housing that defines a cartridge receiving chamber, and a motor driven fan mounted in the housing. A cartridge, which includes a mass of product capable of being vaporized and a battery for powering the fan, is adapted to be inserted into the cartridge receiving chamber of the housing. When the cartridge is so inserted, the battery is connected to the fan which thus induces air flow through the cartridge, past the mass of product, and out of the housing.

The housing disclosed in the Corris Patent Application is a simple box-like container having an open bottom into which a cartridge is inserted. The container is designed to rest on a horizontal surface such as a table, shelf or the like. Furthermore, contacts for connecting the battery to the motor-driven fan are mounted on one interior wall of the housing out of the path of air flow conducted through the cartridge receiving cavity.

U.S. Pat. No. 4,035,451 (Tringali), also assigned to the assignee of the present invention, discloses a refinement of the Corris system. The Tringali system includes a cartridge which contains both a battery and a support of strip material in which a product to be vaporized is impregnated. The strip material has a convoluted configuration to expose a large amount of its surface area to air currents. This cartridge may be inserted into a simple housing having two sections hinged at one edge in clamshell fashion. The housing, therefore, occupies significantly more lateral space when one of its sections is opened from the other than it does when closed. The Tringali system also includes electrical contacts for connecting the battery to a motor-driven fan and structure for supporting the cartridge.

U.S. Pat. No. 3,522,935 (Lewis) discloses an air treatment device which has an oscillating vane that effects a steady current of air over a wick which projects out of the container of liquid deodorant. This device is housed in a wall mounted container having a removable front cover.

SUMMARY OF THE INVENTION

In a preferred embodiment, to be described below in detail, the apparatus of the present invention induces air flow past a product which is capable of being vaporized. The apparatus is designed for use with a self-contained, replaceable and disposable cartridge holding both the product and a battery for powering the apparatus and includes a compact housing in which the operating components of the apparatus as well as the cartridge are mounted. The housing may be mounted on any vertical surface, such as a wall, and has an easily reached interior providing access to the operating components or for replenishing exhausted product and battery. More particularly, the apparatus occupies the same space whether its housing is open or closed and, therefore, may be mounted in many locations which could not accommodate other apparatus that open into larger or different spaces than that occupied when closed.

The apparatus of the present invention also includes a cylindrical shroud which supports and directs air flow through the cartridge. An electrical contact is associated with the shroud to positively connect the cartridge-contained battery to the apparatus without obstructing air flow through the cartridge.

The housing comprises a hollow outer housing shell and a hollow, generally cylindrical inner housing shell, having an axis, in which the operating components of the apparatus, namely a motor and fan, are mounted. The inner shell is mounted for pivoted movement on its axis in the outer shell by a hinge so that it may be opened or closed. When closed, the inner shell compliments the outer shell and thus defines an enclosed component-shielding space. When open, the inner shell is nested within the outer shell to expose the apparatus components. A cartridge may be inserted into or removed from the apparatus when the housing is open.

The apparatus motor and fan are mounted in a cylindrical shroud that is secured to the interior of the inner shell and protects the fan blades. The shroud is open or apertured at the top and bottom to permit air flow axially therethrough.

An electrical contact member, formed of resilient yet torsion-resistant conductive wire has its major dimension spanning the open end of the shroud and a projection from this major dimension for contacting one terminal of the battery when the cartridge is inserted in the apparatus. An integral anchor length extends at an angle from the major dimension of the contact member at a location remote from the projection and is secured to a side wall of the shroud at more than one spaced location. Accordingly, the projection is held in an upright position for contacting the one terminal of the power source.

Accordingly, it is an object of the present invention to provide a housing for an apparatus that induces air flow past a product capable of being vaporized which is compact and easily operated. Another object of the present invention is to provide a support which accurately locates a battery and product-containing cartridge. Moreover, this support is associated with an electrical contact which reliably connects with the battery terminals to the operating components of the apparatus.

Other objects, aspects and advantages of the present invention will be pointed out in or will be understood from the following detailed description provided below in conjunction with the accompanying drawings.

BRIEF DESCRIPTION OF THE DRAWINGS

FIG. 1 is a perspective view of the apparatus of the present invention for inducing air flow past a product which is capable of being vaporized. The housing is shown in its closed position with the inner and outer housing shells complimentary to one another.

FIG. 2 is a vertical cross-sectional view taken through plane 2—2 in FIG. 1 illustrating the housing in its closed position as well as its internal components in detail.

FIG. 3 is a horizontal cross-sectional view taken through discontinuous plane 3—3 in FIG. 2 looking downwardly again illustrating the housing in its closed position.

FIG. 4 is a vertical cross-sectional view similar to that shown in FIG. 2 with the inner housing shell nested in the outer housing shell.

FIG. 5 is a horizontal cross-sectional view taken through discontinuous plane 5—5 in FIG. 4 looking downwardly also illustrating the inner shell nested in the outer shell.

FIG. 6 is a partial perspective view of the motor and fan containing shroud structure and of the electrical contact positioned for connection with one terminal of a battery housed in a cartridge.

DETAILED DESCRIPTION OF THE PREFERRED EMBODIMENT

FIG. 1 illustrates the apparatus of the present invention for inducing air flow past a product which is capable of being vaporized. The product is held in a cartridge along with a source of power, in the form of a battery, for components of the apparatus. The cartridge is advantageously made in accordance with U.S. Pat. No. 4,035,451 (Tringali) which is incorporated herein by reference.

The apparatus, generally indicated at 10, further includes various internal components which are described below in detail, and are housed in a housing indicated at 12. The housing comprises an outer housing shell 13 which is partially cylindrical in shape, having a flat back wall 16 adapted to engage a wall or other vertical surface on which the apparatus may be mounted, and top and bottom walls 18 and 20 respectively. As can be seen in FIGS. 2 and 3, two holes 22 are disposed through the back wall 16 to provide access for hangers to complete a wall mount. Open grills 24 and 26 are respectively disposed in the top and bottom walls 18 and 20.

The outer shell is partially cylindrical by virtue of a plane extending parallel to its axis A, which intersects it to define an open front face 28.

The housing 12 is completed by an inner housing shell 30, which is also partially cylindrical since it too has an open face 31. The inner shell further has a diameter and a height both smaller than that of the outer shell 14 and is formed with a flat front wall 32 and top and bottom walls 34 and 36 respectively. Further, open grills 38 and 40 are respectively disposed in the top and bottom walls 34 and 36 of the inner shell 30.

The inner shell 30 is mounted with the outer shell 14 and is received in the open face 28 thereof by means of a hinge arrangement. The mounting positions the inner shell to compliment the outer shell when in a closed position shown in FIGS. 1 through 3 and further to be nested within the outer shell when in an open position as shown in FIGS. 4 and 5. The hinge arrangement comprises two hinge pins 42 and 44 respectively formed on the upper and lower walls 34 and 36 of the inner shell 30. Each pin is received in an appropriate hinge hole 46 and 48 respectively formed in the upper and lower walls 18 and 20 of the outer shell 14 a substantial distance from the shell sidewall. The hinge pins are substantially equidistant from the side wall of the inner shell, substantially collinear with the axis B of the inner shell, but are not necessarily collinear with the outer shell axis A. The inner shell may be pivoted between open and closed positions complimenting the outer shell and nested within the outer shell providing the axis of the hinge arrangement, that is axis B, is spaced from the outer shell back wall 16 by a distance greater than the diameter of the inner shell. Accordingly, when opened to gain access to the internal components of the apparatus, the housing occupies the same space which it occupies in its closed configuration. Therefore, the apparatus may be mounted in areas where an apparatus having a housing which opens through a conventional side mounted hinge could not be used.

The housing 12 has a detent arrangement for holding the inner shell in closed position relative to the outer shell. As shown in detail in FIG. 3, the inner surface 50 of the outer housing shell 14 is formed with notches 52 extending in the axial direction at locations adjacent the open faces 28 thereof. Mating radially outwardly extending ribs 54 are formed at the margin of the inner shell adjacent the open face 31 thereof, and may be received in notches 52. This interengaging rib and notch arrangement holds the inner shell in its closed position relative to the outer shell during operation of the apparatus.

As shown in FIGS. 2 and 4, the internal operating components of the apparatus of the present invention include a C-shaped mounting bracket 56 which is positioned on the inside of the flat front wall 32 of inner housing shell 30 by two locating pins 58 and 60. A rivet or other fastener 62 secures the mounting bracket to the front face. A shroud structure, generally indicated at 64, is mounted by means of two screws 66 on the lower leg 68 of the C-shaped bracket 56, and comprises a small diameter, lower cylindrical section 70 in which a 1.5 volt D.C. electric motor 72 is craddled. Screws 66 clamp the bottom wall 74 of section 70 to the leg 68 by being tapped into the motor housing.

A radially outwardly directed flange 76 having apertures 78 (FIG. 5) is integrally formed with cylindrical section 70 and a larger diameter cylindrical shroud 79 extends upwardly therefrom. This shroud shields the blades of a fan 80 which is mounted for rotation with the shaft 82 of motor 72. An upper support flange 84 extends radially outwardly from the upper margin of shroud 79 and is bounded by a partially cylindrical wall 86 located toward the flat front wall 32 of inner housing member 30.

The negative terminal of motor 72 is connected by a lead 88 to a spring contact 90 fastened to the upper leg 92 of the C-shaped bracket 56. Alternatively, if conductive, the bracket 56 can directly serve as lead 88.

The positive terminal of motor 72 is similarly connected by a lead 94 to a spring contact member 96 which spans the open upper end of shroud 79. Contact member 96 is formed of a resilient yet torsion-resistant conductive wire. Moreover, its major dimension extends diametrically across the shroud. At least one projection 98 is formed of the contact member, for example, by bending as shown in FIG. 9, or is otherwise attached thereto to extend vertically upwardly. Further, the contact member has two anchor lengths 100 which extend parallel to axes A and B at an angle to the major dimension of the contact member down the outside surface of the shroud 79.

As can be seen in FIG. 2, the contact member passes through two diametrically opposing slots 102 in the shroud 79 and extends downwardly on the outside of the shroud from the slots through its anchor lengths 100. Each of the anchor lengths has a bottom, inwardly bent short leg 104 which passes into the shroud wall through opposing slots 106, each of which is directly beneath one of the slots 102. Accordingly, each anchor length 100 of the contact member 96 is secured to the shroud at two spaced locations, namely at slots 102 and 106. Therefore, since contact member is torsion resistant, its projection is held in an upright position. By virtue of the contact member's material, bending to either side is resisted. Finally, the contact member extends generally perpendicularly to the open face 31 of inner shell 30. Therefore, a cartridge inserted into the housing moves along the major dimension of the contact member minimizing torsion forces thereon. Since the member is inextensible, forces exerted in this direction tend to distort it less than forces exerted perpendicularly to the major dimension. Thus, the projection is self-positioning in the shroud for contact with an appropriate power source.

It can also be seen that contact member 96 presents little obstruction to air flow created through the shroud 79 and the cartridge. In particular, the projection and the anchor lengths define a single plane which extends in the direction of air flow created by the fan through the housing and cartridge.

The apparatus of the present invention is designed for use with a cartridge, such as that disclosed in U.S. Pat. No. 4,035,451 (Tringali), generally indicated at 108, which comprises a cartridge housing 110 that supports a power source in the form of a battery 112 in its center. The cartridge has top and bottom covers 114 and 116 respectively. The top cover 114 is supported on support flange 84 when received in the apparatus as shown in FIG. 2. Moreover, the cartridge is precisely positioned on the flange 84 since its movement into the apparatus is limited by the cylindrical wall 86. Further, when the cartridge is fully inserted to abut the cylindrical wall 86, the contact member 96 makes firm electrical connection with the positive terminal 118 of battery 112 exposed through a suitable hole 120 in the top cartridge wall. Similarly, the negative terminal 122 of the battery is electrically connected to contact 90. Therefore, when the cartridge is received in the apparatus, the motor 72 is connected to battery 112 to rotate the fan 80.

As disclosed in the Tringali Patent noted above, the cartridge also includes an annular space in which a product capable of being vaporized is mounted. For example, this product may be impregnated in a support strip of microporous material to be vaporized therefrom.

As can be seen in FIG. 2, air flow is conducted into the apparatus housing through grills 28 and 40 in the outer and inner housing shells respectively at their lower end. The air flow is subsequently conducted by the fan through the shroud 79, through the cartridge 108, over the product, and subsequently out of the housing through grills 26 and 38.

From the above description it can be seen that the apparatus of the present invention incorporates several beneficial features. First, this apparatus is housed in a construction which may be closed or opened in the same space. Therefore, it may be installed in areas where space is limited.

When open, the cartridge may be inserted or removed from the apparatus easily. As shown in FIG. 2, the contacts for making electrical connection with the battery and the cartridge are self-positioning. Further, the contact member 96 is oriented so that when inserted or withdrawn from the housing, cartridge 108 moves in the direction of the major direct dimension thereof. Therefore, the contact resists displacement from its proper position for making electrical connection with the positive battery terminal 118. Further, the cartridge is precisely positioned by the cylindrical wall 86 so that air flow is properly conducted past the product which is contains as well as so that the battery is correctly connected with the motor for driving fan 80.

Accordingly, although a specific embodiment of the present invention has been described above in detail, it is to be understood that this is for purposes of illustration. Modifications may be made to the described structure by those skiled in the art in order to adapt this apparatus for inducing air flow past a product capable of being vaporized to particular applications.

What is claimed is:

1. Improved means for mounting a cartridge, which carries a product capable of being vaporized and a battery and is used in conjunction with apparatus including battery-powered means operative to induce air flow past said product when said cartridge is mounted on said mounting means; said improved cartridge mounting means supporting said cartridge, connecting one terminal of said battery to said battery-powered means, and comprising:

A. support means including
  1. a tubular member
  2. flange means projecting radially from one margin of said tubular member for receiving and supporting said cartridge, and
  3. a partially cylindrical wall extending axially from said flange means for positioning said cartridge when received and supported on said flange means, and B. a contact member formed of resilient yet torsion resistant conductive wire having
  1. a first section spanning said tubular member at said one margin;
  2. a projection from said first section for contacting said one terminal of said battery when said cartridge is received and supported on said flange means; and
  2. at least one anchor length extending along the side wall of said tubular member and being secured thereto at at least two spaced locations whereby bending of said projection is resisted by said anchor length and whereby said contact presents minimal obstruction to flow through said tubular member and said cartridge.

2. The improved cartridge mounting means as claimed in claim 1 wherein said tubular member comprises a cylindrical shroud having two at least partially open ends and wherein said flange means comprises a flange projecting radially from said shroud at one of said ends.

3. The improved cartridge mounting means as claimed in claim 2 wherein said partially cylindrical wall extends axially from a radially outer margin of said flange for positioning the cartridge when engaged on said flange.

4. The improved cartridge mounting means as claimed in claim 2 wherein said first section of said contact member spans one open end of said shroud and said anchor length extends axially along the side wall of said shroud.

5. The improved cartridge mounting means as claimed in claim 4 wherein said contact member further comprises a second anchor length extending from said first section of said contact member axially along the side wall of said shroud at a location diametrically opposed to said first anchor length, and also being secured to said shroud at at least two spaced locations.

6. The improved cartridge mounting means as claimed in claim 1 wherein said conductive wire is bent to integrally form said projection and said anchor length of said contact member.

7. The improved cartridge mounting means as claimed in claim 1 wherein said conductive wire is bent to integrally form said projection and said anchor length of said contact member so that said wire defines a single plane.

8. The improved cartridge mounting means as claimed in claim 7 wherein said single plane extends generally parallel to the direction of air flow induced past the product so as to present minimal obstruction to the air flow.

9. The improved cartridge mounting means as claimed in claim 1 wherein said first section of said contact member extends in the direction along which a cartridge is received on said flange means.

10. In a system for inducing air flow past a product capable of being vaporized, mounted in a cartridge along with a battery, that includes a housing, battery-powered means mounted within the housing for inducing said air flow and cartridge mounting means mounted within said housing for supporting said cartridge therein and for connecting one terminal of said battery to said battery-powered means, the improvements wherein:

A. said housing comprises
  1. an inner housing shell having an axis, said battery-powered means and said cartridge mounting means being mounted with said inner housing shell;
  2. an outer housing shell; and
  3. hinge means for mounting said inner housing shell within said outer housing shell for shiftable pivoted movement substantially on said axis between a closed operating position complementary to said outer housing shell and an open servicing position nested within said outer housing shell, said outer housing shell cooperating with said inner housing shell in the closed position thereof to enclose said battery-powered means, said cartridge mounting means and said cartridge, said outer housing shell cooperating with said inner housing shell in the open position thereof to render said battery-powered means, said cartridge mounting means and said cartridge accessable for removal, replacement and servicing, and wherein B. said cartridge mounting means comprises
  1. support means including a tubular member, flange means projecting radially from one margin of said tubular member for receiving and supporting said cartridge, and a partially cylindrical wall extending axially from said flange means for positioning said cartridge when received and supported on said flange means, and
  2. a contact member formed of resilient yet torsion resistant conductive wire having a first section spanning said tubular member at said one margin; a projection from said first section for contacting said one terminal of said battery when said cartridge is received and supported on said flange means; and at least one anchor length extending along the side wall of said tubular member and being secured thereto at at least two spaced locations whereby bending of said projection is resisted by said anchor length and whereby said contact presents minimal obstruction to air flow through said tubular member and said cartridge.

11. The improved system as claimed in claim 10 wherein said tubular member comprises a cylindrical shroud having two at least partially open ends and wherein said flange means comprises a flange projecting radially from said shroud at one of said ends.

12. The improved system as claimed in claim 11 wherein said partially cylindrical wall extends axially from a radially outer margin of said flange for positioning the cartridge when engaged on said flange.

13. The improved system as claimed in claim 11 wherein said first section of said contact member spans one open end of said shroud and said anchor length extends axially along the side wall of said shroud.

14. The improved system as claimed in claim 13 wherein said contact member further comprises a second anchor length extending from said first section of said contact member axially along the side wall of said shroud at a location diametrically opposed to said first anchor length, and also being secured to said shroud at at least two spaced locations.

15. The improved system as claimed in claim 10 wherein said conductive wire is bent to integrally form said projection and said anchor length of said contact member.

16. The improved system as claimed in claim 10 wherein said conductive wire is bent to integrally form said projection and said anchor length of said contact member so that said wire defines a single plane.

17. The improved system as claimed in claim 16 wherein said single plane extends generally to the direction of air flow induced past the product so as to present minimal obstruction to the air flow.

18. The improved system as claimed in claim 10 wherein said first section of said contact member extends in the direction along which a cartridge is received on said flange means.

19. The improved system as claimed in claim 10 wherein said outer housing shell is generally cylindrical and has a larger diameter and height than said inner housing shell.

20. The improved system as claimed in claim 10 further comprising:

detent means for holding said inner housing shell in said closed position complementary to said outer housing shell.

21. The improved system as claimed in claim 20 wherein said detent means comprises a recess formed in one of said inner and outer housing shells; and a projection formed on the other of said inner and outer housing shells at a location to be received in said recess when said inner housing shell is in said closed position complementary to the outer housing shell.

22. The improved system as claimed in claim 10 wherein at least one of said inner and said outer housing shells is formed with an opening at one end and at least one of said inner and outer housing shells is formed with an opening at the axially opposed end to permit air flow axially through the space enclosed by said housing.

23. The improved system as claimed in claim 10 wherein said inner and outer housing shells each have top, bottom and side walls, said top and bottom outer housing shell walls being spaced by a distance greater than said top and bottom inner housing walls and wherein said hinge means comprises first and second pin receiving apertures formed respectively in said top and bottom outer housing shell walls adjacent said open face and being a substantial distance from said outer shell side wall; and first and second hinge pins formed respectively in said top and bottom inner housing shell walls, being substantially equidistant from said inner shell side wall and received respectively in said first and second apertures for pivoting movement therein.

* * * * *